(12) United States Patent
Fürstner et al.

(10) Patent No.: US 6,180,656 B1
(45) Date of Patent: Jan. 30, 2001

(54) USE OF CONDENSATED (HETARYL-SUBSTITUTED) 1-BENZAL-3-PYRAZOL DERIVATES FOR TREATING SPECIAL DISEASES OF THE CARDIOVASCULAR AND THE CENTRAL NERVOUS SYSTEMS

(75) Inventors: Chantal Fürstner, Ruhr; Alexander Straub, Wuppertal; Ulrich Niewöhner, Wermelskirchen; Thomas Jaetsch, Köln; Achim Feurer, Odenthal; Raimund Kast, Wuppertal; Johannes-Peter Stasch, Solingen; Elisabeth Perzborn, Wuppertal; Joachim Hütter, Wuppertal; Klaus Dembowsky, Schriesheim, all of (DE)

(73) Assignee: Bayer Aktiengesellschaft, Leverkusen (DE)

(*) Notice: Under 35 U.S.C. 154(b), the term of this patent shall be extended for 0 days.

(21) Appl. No.: 09/284,032

(22) PCT Filed: Oct. 1, 1997

(86) PCT No.: PCT/EP97/05381

§ 371 Date: Apr. 6, 1999

§ 102(e) Date: Apr. 6, 1999

(87) PCT Pub. No.: WO98/16223

PCT Pub. Date: Apr. 23, 1998

(30) Foreign Application Priority Data

Oct. 14, 1996 (DE) .............................. 196 42 255

(51) Int. Cl.[7] ...................... A61K 31/415; C07D 231/10
(52) U.S. Cl. ...................... 514/406; 548/374.1
(58) Field of Search .................. 548/374.1; 514/406

(56) References Cited

FOREIGN PATENT DOCUMENTS 470039 2/1992 (EP) .
667345 8/1995 (EP) .

OTHER PUBLICATIONS

S.–M. Yu et al.: Inhibition of Platelet Function by A02131.1, a Novel Inhibitor. . . blood, vol. 87, No. 9, May 1, 1996, pp. 3758–3767.

C.–C Wu et al.: "YC–1 inhibited human platelet aggregation through. . . cyclase", British Journal of Pharmacology, vol. 116, No. 3, 1995, pp. 1973–1978.

F.–N. Ko et al. "YC–1, a Novel Activator of Platelet Guanylate Cyclase", Blood, vol. 84, No. 12, Dec. 15, 1994, pp. 4226–4233.

*Primary Examiner*—Raymond Henley, III
(74) *Attorney, Agent, or Firm*—Norris McLaughlin & Marcus P.A.

(57) ABSTRACT

The present invention relates to the new use of 1-benzyl-3-(substituted hetaryl)-fused pyrazole derivatives, some of which are known, of the general formula (I)

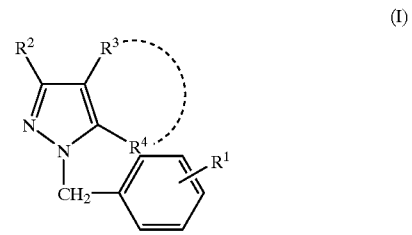

(I)

in which $R^1$ to $R^4$ have the meaning indicated in the description, as medicaments, and to new active compounds, in particular to their use as vasodilators, if appropriate in combination with organic nitrates and NO donors and if appropriate in combination with compounds which inhibit the degradation of cGMP.

14 Claims, No Drawings

USE OF CONDENSATED (HETARYL-SUBSTITUTED) 1-BENZAL-3-PYRAZOL DERIVATES FOR TREATING SPECIAL DISEASES OF THE CARDIOVASCULAR AND THE CENTRAL NERVOUS SYSTEMS

This is a 371 of PCT/EP97/05381 filed Oct. 1, 1997.

The present invention relates to the new use of 1-benzyl-3-(substituted hetaryl)-fused pyrazole derivatives, some of which are known, as medicaments, and to new active compounds, in particular to their use as vasodilators, if appropriate in combination with organic nitrates and NO donors and if appropriate in combination with compounds which inhibit the degradation of cGMP.

It is already known that 1-benzyl-3-(substituted hetaryl)-fused pyrazole derivatives inhibit stimulated platelet aggregation in vitro (cf. EP-667 345 A1; C. -C. Wu et al., Br. J. Pharmacol. 1995; 116: 1973–1978; F. -N. Ko et al., Blood 1994; 84: 4226–4233; S. -U. Yu et al., Blood 1996, 87: 3758–3767).

It has now surprisingly been found that 1-benzyl-3-(substituted hetaryl)-fused pyrazole derivatives of the general formula (I)

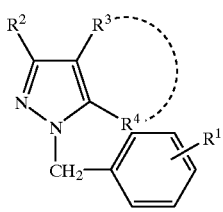

in which
R$^1$ represents hydrogen, halogen, hydroxyl or C$_1$–C$_3$-alkyl or C$_1$–C$_3$-alkoxy,
R$^2$ represents a radical of the formula

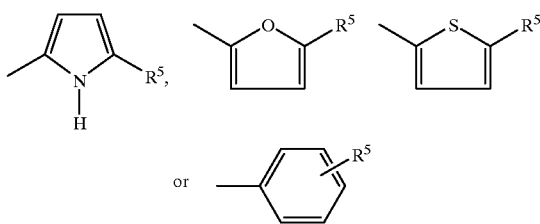

in which
R$^5$ denotes hydrogen, halogen, carboxyl, C$_1$–C$_3$-alkyl, C$_1$–C$_3$-alkoxy carbonyl or a radical of the formula —CH$_2$—OR$^6$,
in which
R$^6$ denotes hydrogen or C$_1$–C$_3$-alkyl,
R$^3$ and R$^4$ together form a radical of the formula

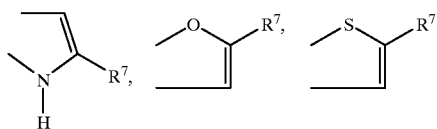

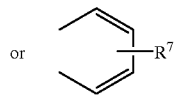

in which
R$^7$ denotes hydrogen, halogen, hydroxyl, C$_1$–C$_3$-alkyl or C$_1$–C$_3$-alkoxy,
and their isomeric forms and salts,
besides their weak antiaggregatory properties exhibit a marked vasodilatory action, in particular a lowering of blood pressure. They are thus suitable for the treatment of specific disorders of the cardiovascular system, in particular for the treatment of various forms of angina pectoris, of myocardial infarct, of cardiac insufficiency, of arteriosclerosis, stroke and of hypertension.

The compounds of the general formula (I) according to the invention can also be present in the form of their salts. In general, salts with organic or inorganic bases or acids may be mentioned here.

In the context of the present invention, physiologically acceptable salts are preferred. Physiologically acceptable salts can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalene-disulphonic acid, acetic acid, propionic acid, lactic acid, tartaric acid, citric acid, fumaric acid, maleic acid or benzoic acid.

Physiologically acceptable salts can likewise be metal or ammonium salts of the compounds according to the invention if they have a free carboxyl group. Particularly preferred salts are, for example, sodium, potassium, magnesium or calcium salts, and also ammonium salts which are derived from ammonia, or organic amines such as, for example, ethylamine, di- or triethylamine, di- or triethanolamine, dicyclohexylamine, dimethylaminoethanol, arginine, lysine or ethylenediamine.

In the context of the invention, C$_1$–C$_3$-alkyl represents a straight-chain or branched hydrocarbon radical having 1 to 3 carbon atoms. Examples which may be mentioned are: methyl, ethyl, propyl and isopropyl.

In the context of the invention, C$_1$–C$_3$-alkoxy represents a straight-chain or branched alkoxy radical having 1 to 3 carbon atoms. Examples which may be mentioned are: methoxy, ethoxy, propoxy and isopropoxy.

In the context of the invention, C$_1$–C$_3$-alkoxycarbonyl represents a straight-chain or branched alkoxycarbonyl radical having 1 to 3 carbon atoms. Examples which may be mentioned are: methoxycarbonyl, ethoxycarbonyl, propoxycarbonyl and isopropoxycarbonyl.

Preferably, compounds of the general formula (I) according to the invention
in which
R$^1$ represents hydrogen, fluorine, chlorine, C$_1$–C$_3$-alkyl or C$_1$–C$_3$-alkoxy, $R^2$ represents a radical of the formula

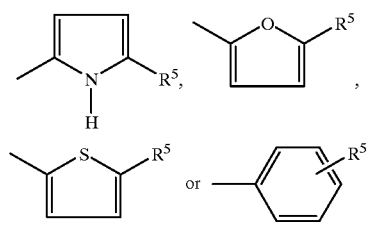

in which
$R^5$ denotes hydrogen, chlorine, carboxyl, $C_1$–$C_3$-alkyl, $C_1$–$C_3$-alkoxycarbonyl or a radical of the formula —$CH_2$—$OR^6$,
in which
$R^6$ denotes hydrogen or methyl,
$R^3$ and $R^4$ together form a radical of the formula

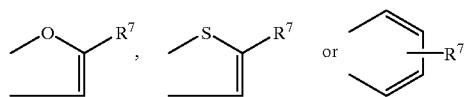

in which
$R^7$ denotes hydrogen, fluorine, chlorine, $C_1$–$C_3$-alkyl or $C_1$–$C_3$-alkoxy, and their isomeric forms and salts, are used for the treatment of specific cardiovascular disorders.

Particularly preferably, compounds of the general formula (I) according to the invention
in which
$R^1$ represents hydrogen, fluorine, chlorine or methoxy,
$R^2$ represents a radical of the formula

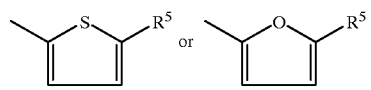

in which
$R^5$ denotes hydrogen, $C_1$–$C_3$-alkyl or a radical of the formula —$CH_2$—$OR^6$,
in which
$R^6$ denotes hydrogen or methyl,
$R^3$ and $R^4$ together form a radical of the formula

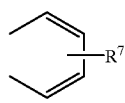

in which
$R^7$ denotes hydrogen, chlorine, fluorine, methyl or methoxy, and their isomeric forms and salts, are used for the treatment of specific cardiovascular disorders.

The invention additionally relates to new substances which are listed in the following table:

TABLE

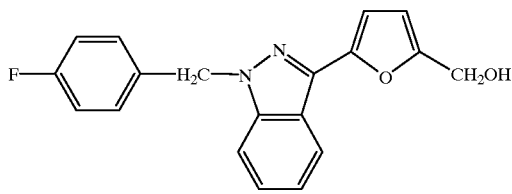

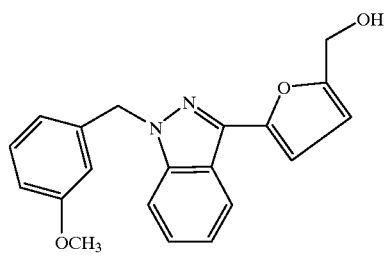

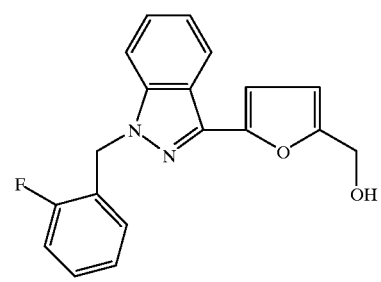

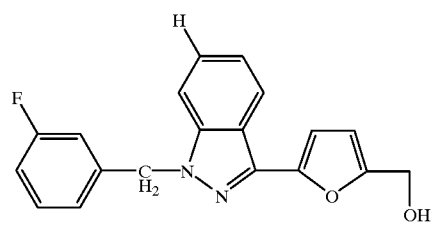

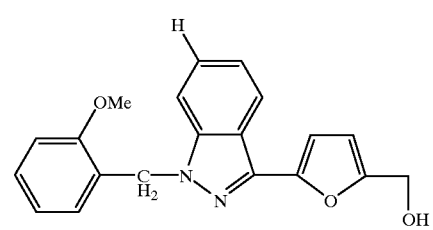

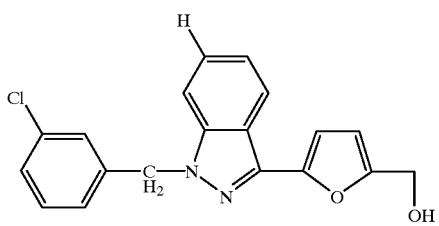

TABLE-continued

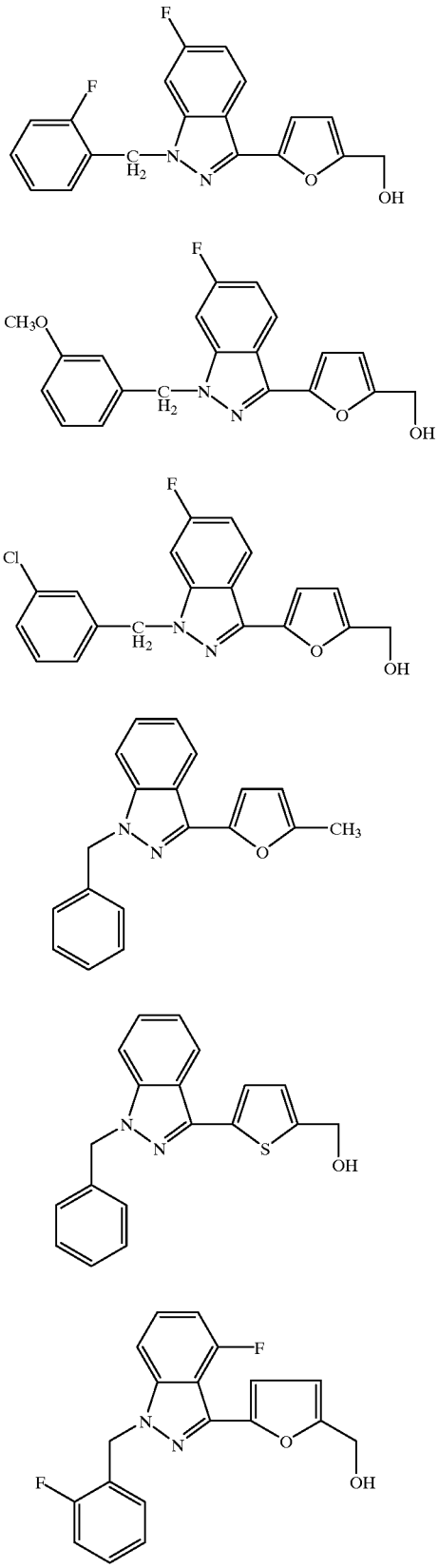

TABLE-continued

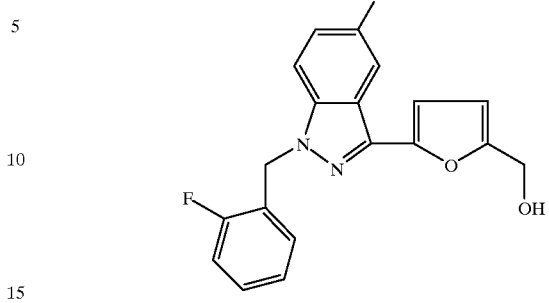

The known and new compounds of the general formula (I) according to the invention can be prepared by customary methods, e.g. according to EP-667 345 A1.

Moreover, the invention preferably also includes the combination of the compounds of the general formula (I) according to the invention and of the new substances with organic nitrates and NO donors.

Organic nitrates and NO donors in the context of the invention are in general substances which display their therapeutic action via the release of NO or NO species. Sodium nitroprusside (SNP), nitroglycerine, isosorbide dinitrate, isosorbide mononitrate, molsidomine and SIN-1 and similar substances are preferred.

The invention additionally includes the combination with compounds which inhibit the degradation of cyclic guanosine monophosphate (cGMP). These are in particular inhibitors of the phosphodiesterases 1, 2 and 5; nomenclature according to Beavo and Reifsnyder (1990) TIPS 11 pp. 150–155. By means of these inhibitors, the action of the compounds according to the invention is potentiated and the desired pharmacological effect is increased.

The new and known compounds of the general formula (I) to be used according to the invention exhibit an unforeseeable, valuable spectrum of pharmacological action. They induce, for example, a vasorelaxation and lead to a lowering of blood pressure and increase in the coronary blood flow.

They are thus suitable for use in the treatment of specific disorders of the cardiovascular system such as, for example, the various forms of angina pectoris, of myocardial infarct, of cardiac insufficiency, of arteriosclerosis, stroke and of hypertension.

To determine the cardiovascular action, the following investigations were carried out: in in vitro investigations on cells of vascular origin, the influence on guanylate cyclase-dependent cGMP formation was tested with and without NO donors. The vasorelaxant action was determined on rabbit aorta rings precontracted with phenylephrine. The hypotensive action was investigated in anaesthetized rats.

Stimulation of Soluble Guanylate Cyclase in Primary Endothelial Cells

Primary endothelial cells were isolated from pig aortas by treatment with collagenase soln. The cells were then cultured in culture medium until confluence was achieved. For the investigations, the cells were passaged, inoculated into cell culture plates and subcultured until confluence was achieved. To stimulate the endothelial guanylate cyclase, the culture medium was aspirated and the cells were washed once with Ringer's solution and incubated in stimulation buffer with or without NO donor (sodium nitroprusside, SNP, 1 μM). Following this, the test substances (final concentration 1 µM) were then pipetted onto the cells. After the end of the incubation time of 10 minutes, the buffer solution was aspirated and the cells were lysed at −20° C. for 16 hours. The intracellular cGMP was then determined radioimmunologically.

TABLE A

| Ex No. | % cGMP increase (NOSYNTH) |
|---|---|
| 1 | >1000 |
| 2 | 72 |
| 3 | 250 |
| 4 | 413 |
| 7 | 734 |
| 8 | 28 |
| 10 | 238 |
| 11 | 14 |
| 14 (YC-1) EP 667 345 Al | >906 |

Vasorelaxant Action in vitro 1.5 mm wide rings of an isolated rabbit aorta are placed individually under a pretension into 5 ml organ baths containing carbogen-aerated Krebs-Henseleit solution at a temperature of 37° C. The contractile force is amplified and digitalized, and recorded in parallel on a linear recorder. To generate a contraction, phenylephrine is added to the bath cumulatively in increasing concentration.

After several control cycles, the substance to be investigated is investigated in each further passage in increasing dose in each case and the contraction is compared with the height of the contraction achieved in the last previous passage. From this, the concentration is calculated which is necessary to reduce the height of the control value by 50% ($IC_{50}$). The standard administration volume is 5 µl.

TABLE B

| Ex. No. | Aorta IC 50 (µM) |
|---|---|
| 1 | 4.1 |
| 3 | 16 |
| 4 | 9.2 |
| 14 (YC-1) EP 667 345 A | 10 |

Blood Pressure Measurements on Anaesthetized Rats

Male Wistar rats having a body weight of 300–350 g are anaesthetized with thiopental (100 mg/kg i.p.). After tracheotomy, a catheter is inserted in the femoral artery for blood pressure measurement. The substances to be tested are administered orally in various doses as a suspension in Tylose solution by means of stomach tube.

TABLE C

| Ex. No. | Dose | Max. blood pressure decrease | Time |
|---|---|---|---|
| 1 | 10 mg/kg | −14 mm Hg | 60 min |
|  | 30 mg/kg | −18 mm Hg | 60 min |
| 14 (YC-1) | 10 mg/kg | −10 mm Hg | 60 min |
| EP 667 345 Al | 30 mg/kg | −18 mm Hg | 60 min |

The compounds described in the present invention are also active compounds for the control of illnesses in the central nervous system which are characterized by disorders of the NO/cGMP system. In particular, they are suitable for the elimination of cognitive deficits, for the improvement of learning and memory disorders and for the treatment of Alzheimer's disease. They are also suitable for the treatment of disorders of the central nervous system such as anxiety, tension and depressive states, sexual dysfunctions and sleep disorders caused by the central nervous system, and for the regulation of pathological disorders in food, semi-luxury food and addictive drug intake.

Furthermore, these active compounds are also suitable for the regulation of the cerebral circulation and are thus effective agents for the control of migraine.

They are also suitable for the prophylaxis and control of the sequelae of cerebral infarcts (cerebral apoplexy) such as stroke, cerebral ischaemias and of cranio-cerebral trauma. The compounds according to the invention can likewise be employed for the control of states of pain.

The present invention includes pharmaceutical preparations which, besides non-toxic, inert pharmaceutically suitable excipients, contain one or more compounds according to the invention or which consist of one or more active compounds according to the invention, and processes for the production of these preparations.

The active compound(s) can optionally also be present in microencapsulated form in one or more of the excipients indicated above.

The therapeutically active compounds should be present in the abovementioned pharmaceutical preparations in a concentration of approximately 0.1 to 99.5, preferably of approximately 0.5 to 95% by weight of the total mixture.

Apart from the compounds according to the invention, the pharmaceutical preparations mentioned above can also contain further pharmaceutical active compounds.

In general, it has proved advantageous both in human and in veterinary medicine to administer the active compound(s) according to the invention in total amounts of approximately 0.5 to approximately 500, preferably 5 to 100, mg/kg of body weight every 24 hours, if appropriate in the form of several individual doses, to achieve the desired results. An individual dose contains the active compound(s) according to the invention preferably in amounts of approximately I to approximately 80, in particular 3 to 30, mg/kg of body weight.

PREPARATION EXAMPLES

Example 1

1-(2-Fluorobenzyl)-3-(5-hydroxymethylfuran-2-yl)-indazole

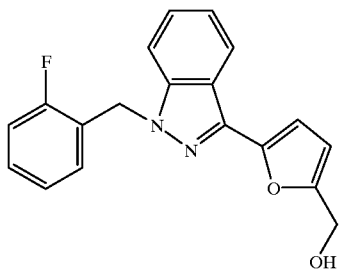

0.8 g(2.5 mmol) of 1-(2-fluorobenzyl)-3-(5-formyl-2-furanyl)-indazole is suspended in 40 ml of propanol and 0.8 g of $NaBH_4$ is added slowly at 0° C. After stirring at room temperature for 1 hour, the clear solution is added to water, the mixture is extracted with ethyl acetate, the organic phase is dried with sodium sulphate and evaporated in vacuo, and the residue is chromatographed on silica gel using, toluene/ethyl acetate mixtures as eluent.

620 mg (77% of theory) of crystals are obtained.

M.p. (melting point): 83° C.

$R_f$ ($SiO_2$, toluene/ethyl acetate 2:1): 0.50

The examples in Tables 1, 2 and 3 were prepared analogously:

TABLE 1

| Ex. No. | Structure | M.p.[1] °C. |
|---|---|---|
| 2 | 2H-isoindole with 3-methoxybenzyl at N and 5-(hydroxymethyl)furan-2-yl substituent | 95 |
| 3 | 1H-indazole with 4-fluorobenzyl at N1 and 3-[5-(hydroxymethyl)furan-2-yl] substituent | 82 |

[1] Melting point

TABLE 2

Indazole core with $R^8$ on N1, $R^9$ on 6-position, and 3-[5-(hydroxymethyl)furan-2-yl] substituent.

| Ex. No. | $R^8$ | $R^9$ | Yield (% of theory) M.p. °C. | $R_f$ |
|---|---|---|---|---|
| 4 | 3-F-C$_6$H$_4$-CH$_2$ | H | 43 / 112 | 0.50 (TEA 1:1) |
| 5 | 2-OMe-C$_6$H$_4$-CH$_2$ | H | 50 / 109 | |
| 6 | 3-Cl-C$_6$H$_4$-CH$_2$ | H | 6 | |
| 7 | 2-F-C$_6$H$_4$-CH$_2$ | F | 65 | |
| 8 | 3-OCH$_3$-C$_6$H$_4$-CH$_2$ | F | 40 / 95 | |
| 9 | 3-Cl-C$_6$H$_4$-CH$_2$ | F | 9 | |

TABLE 3

| Ex. No. | Structure | Yield (% of theory) M.p. ° C. | $R_f$ |
|---|---|---|---|
| 10 | 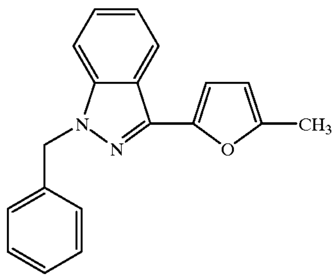 | 92<br>63 | 0.40<br>(H:EA 3:1) |
| 11 | 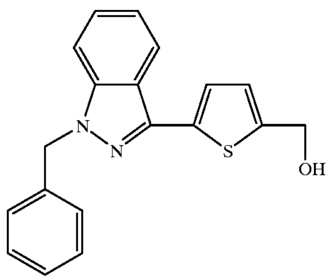 | | |
| 12 | 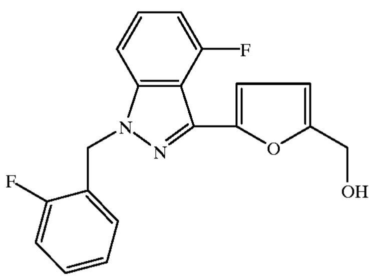 | 89<br>136 | 0.33<br>(H:EA 1:1) |
| 13 | 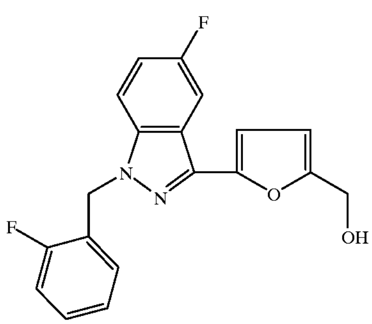 | 83<br>141 | 0.44<br>(H:EA 1:1) |
| 14 | 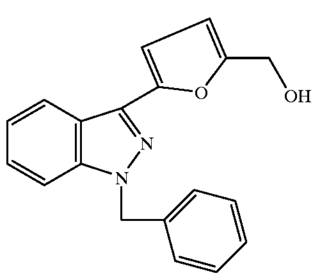 | 112 | |

YC-1 (EP 667345A1)

What is claimed is:

1. A compound selected from the group consisting of:
1-(2-fluorobenzyl)-3-(5-hydroxymethylfuran-2-yl)-indazole,
1-(4-fluorobenzyl)-3-(5-hydroxymethylfuran-2-yl)-indazole,
3-(5-hydroxymethylfuran-2-yl)-1-(3-methoxybenzyl)-indazole,
1-(3-fluorobenzyl)-3-(5-hydroxymethylfuran-2-yl)-indazole,
3-(5-hydroxymethylfuran-2-yl)-1-(2-methoxybenzyl)-indazole,
1-(3-chlorobenzyl)-3-(5-hydroxymethylfuran-2-yl)-indazole,
6-fluoro-1-(2-fluorobenzyl)-3-(5-hydroxymethylfuran-2-yl)-indazole,
6-fluoro-3-(5-hydroxymethylfuran-2-yl)-1-(3-methoxybenzyl)-indazole,
1-(3-chlorobenzyl)-6-fluoro-3-(5-hydroxymethylfuran-2-yl)-indazole,
1-benzyl-3-(5-methylfuran-2-yl)-indazole,
1-benzyl-3-(5-hydroxymethylthiene-2-yl)-indazole,
4-fluoro-1-(2-fluorobenzyl)-3-(5-hydroxymethylfuran-2-yl)-indazole and
5-fluoro-1-(2-fluorobenzyl)-3-(5-hydroxymethylfuran-2-yl)-indazole.

2. A pharmaceutical composition comprising at least one compound according to claim 1, or an isomer or a salt thereof and a pharmaceutically acceptable carrier.

3. A process of preparing the pharmaceutical composition according to claim 2 comprising combining said at least one compound or an isomer or a salt thereof and a pharmaceutically acceptable carrier.

4. Method for treatment of a cardiovascular disorder, said method comprising administering to a patient in need thereof an effective amount therefor of at least one compound according to claim 1 or an isomer or a salt thereof.

5. The method according to claim 4 wherein said cardiovascular disease is hypertension.

6. Method for treatment of a central nervous system disorder, said method comprising administering to a patient in need thereof an effective amount therefor of at least one compound according to claim 1 or an isomer or a salt thereof.

7. A pharmaceutical composition comprising at least one 1-benzyl-3-(subsititued hetaryl)-fused pyrazole derivative of the general formula (I)

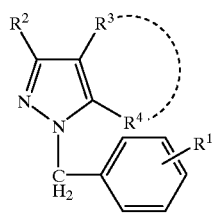

(I)

in which
R$^1$ represents hydrogen, halogen, hydroxyl or C$_1$–C$_3$-alkyl or C$_1$–C$_3$-alkoxy,
R$^2$ represents a radical of the formula

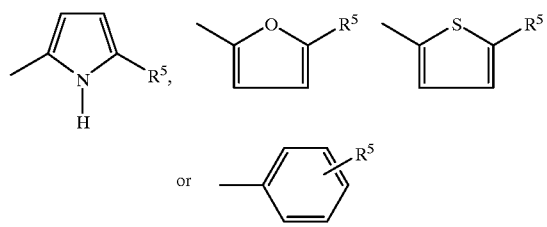

in which
R$^5$ denotes hydrogen, halogen, carboxyl, C$_1$–C$_3$-alkyl, C$_1$–C$_3$-alkoxy carbonyl or a radical of the formula —CH$_2$—OR$^6$,
in which
R$^6$ denotes hydrogen or C$_1$–C$_3$-alkyl,
R$^3$ and R$^4$ together form a radical of the formula

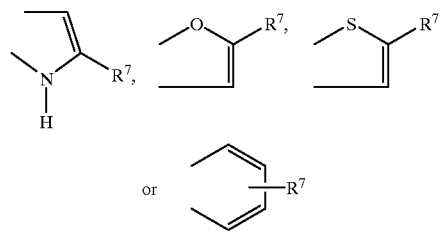

in which
R$_7$ denotes hydrogen, halogen, hydroxyl, C$_1$–C$_3$-alkyl or C$_1$–C$_3$alkoxy,
or an isomer or a salt thereof, organic nitrates and NO donors.

8. A pharmaceutical composition comprising at least one 1-benzyl-3-(subsititued hetaryl)-fused pyrazole derivative of the general formula (I)

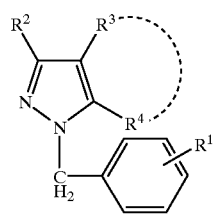

(I)

in which
R$^1$ represents hydrogen, halogen, hydroxyl or C$_1$–C$_3$-alkyl or C$_1$–C$_3$-alkoxy,
R$^2$ represents a radical of the formula

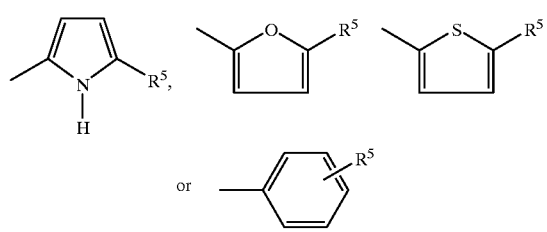

in which $R^5$ denotes hydrogen, halogen, carboxyl, $C_1$–$C_3$-alkyl, $C_1$–$C_3$-alkoxy carbonyl or a radical of the formula —$CH_2$—$OR^6$, in which $R^6$ denotes hydrogen or $C_1$–$C_3$-alkyl, $R^3$ and $R^4$ together form a radical of the formula

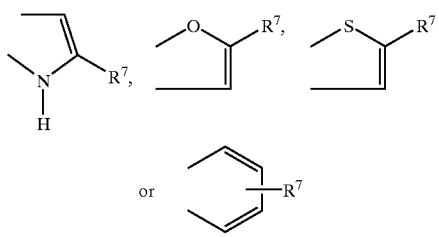

in which $R_7$ denotes hydrogen, halogen, hydroxyl, $C_1$–$C_3$-alkyl or $C_1$–$C_3$alkoxy, or an isomer or a salt thereof and compounds which inhibit the degradation of cGMP.

9. A process of preparing the pharmaceutical composition according to claim 7 comprising combining said at least one 1-benzyl-3-(subsitituted hetaryl)-fused pyrazole derivative, organic nitrates and NO donors.

10. A process of preparing the pharmaceutical composition according to claim 8 comprising combining said at least one 1-benzyl-3-(subsitituted hetaryl)-fused pyrazole derivative and compounds which inhibit the degradation of cGMP and a pharmaceutically acceptable carrier.

11. Method for treatment of a cardiovascular disorder, said method comprising administering to a patient in need thereof an effective amount therefor of at least one 1-benzyl-3-(subsitituted hetaryl)-fused pyrazole derivative of the general formula (I)

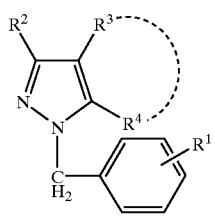

(I)

in which $R^1$ represents hydrogen, halogen, hydroxyl or $C_1$–$C_3$-alkyl or $C_1$–$C_3$-alkoxy, $R^2$ represents a radical of the formula

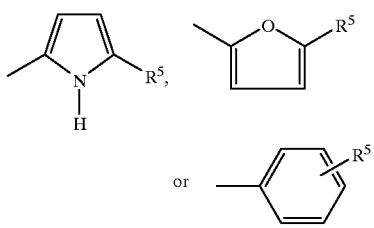

in which $R^5$ denotes hydrogen, halogen, carboxyl, $C_1$–$C_3$-alkyl, $C_1$–$C_3$-alkoxy carbonyl or a radical of the formula —$CH_2$—$OR^6$, in which $R^6$ denotes hydrogen or $C_1$–$C_3$-alkyl, $R^3$ and $R^4$ together form a radical of the formula

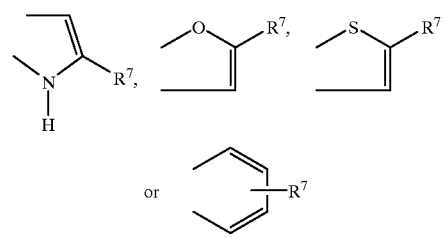

in which $R_7$ denotes hydrogen, halogen, hydroxyl, $C_1$–$C_3$-alkyl or $C_1$–$C_3$alkoxy, or an isomer or a salt thereof.

12. The method according to claim 11 wherein said cardiovascular disease is hypertension.

13. Method for treatment of a central nervous system disorder, said method comprising administering to a patient in need thereof an effective amount therefor of at least one 1-benzyl-3-(subsitituted hetaryl)-fused pyrazole derivative of the general formula (I)

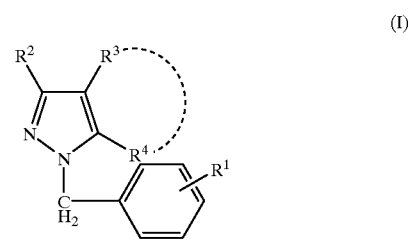

(I)

in which $R^1$ represents hydrogen, halogen, hydroxyl or $C_1$–$C_3$-alkyl or $C_1$–$C_3$-alkoxy, $R^2$ represents a radical of the formula

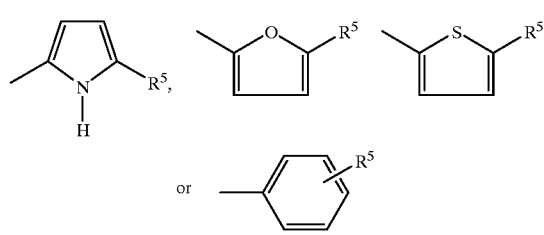

in which $R^5$ denotes hydrogen, halogen, carboxyl, $C_1$–$C_3$-alkyl, $C_1$–$C_3$-alkoxy carbonyl or a radical of the formula —$CH_2$—$OR^6$, in which $R^6$ denotes hydrogen or $C_1$–$C_3$-alkyl, $R^3$ and $R^4$ together form a radical of the formula
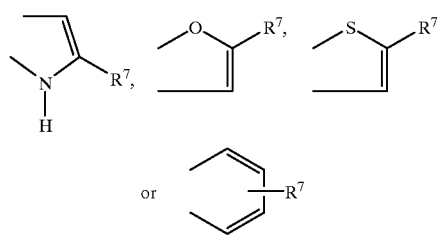
in which
$R_7$ denotes hydrogen, halogen, hydroxyl, $C_1$–$C_3$-alkyl or $C_1$–$C_3$alkoxy,
or an isomer or a salt thereof.
14. The method according to claim 13 wherein said central nervous system disorder is a cerebral infarct.
* * * * *